United States Patent [19]
Deroo

[11] Patent Number: 6,089,870
[45] Date of Patent: Jul. 18, 2000

[54] METHOD FOR AFFIXING A VISUAL ELEMENT ON A DENTAL WORKPIECE

[76] Inventor: David E. Deroo, 5543 N. Indianola Ave., Clovis, Calif. 93611

[21] Appl. No.: 08/959,005

[22] Filed: Oct. 28, 1997

[51] Int. Cl.[7] .................................................. A61C 5/08
[52] U.S. Cl. ............................................................. 433/218
[58] Field of Search ................................. 433/229, 215, 433/218

[56] References Cited

U.S. PATENT DOCUMENTS

| | | | |
|---|---|---|---|
| 2,311,876 | 2/1943 | Scheetz, Jr. ........................... | 156/89.24 |
| 2,512,929 | 6/1950 | Galbraith et al. ........................... | 65/23 |
| 3,658,611 | 4/1972 | Gray ...................................... | 156/89.24 |
| 4,557,693 | 12/1985 | Elggren . | |
| 4,820,160 | 4/1989 | Cohen et al. . | |
| 5,032,449 | 7/1991 | Af Strom ................................ | 428/195 |
| 5,759,039 | 6/1998 | Kunstadter et al. .................... | 433/215 |
| 5,782,638 | 7/1998 | Warren, III et al. ................... | 433/229 |

FOREIGN PATENT DOCUMENTS

| | | | |
|---|---|---|---|
| 8600213 | 1/1986 | WIPO ................................... | 433/229 |

*Primary Examiner*—John J. Wilson
*Attorney, Agent, or Firm*—Worrel & Worrel

[57] ABSTRACT

A method for affixing a visual element on a workpiece, the method including the steps of selecting a visual element to be affixed on the workpiece; treating the visual element so as to render it transferable to the workpiece; transferring the visual element onto the workpiece in a target position; and curing the visual element on the workpiece in the target position so as to affix the visual element in the target position.

4 Claims, 1 Drawing Sheet

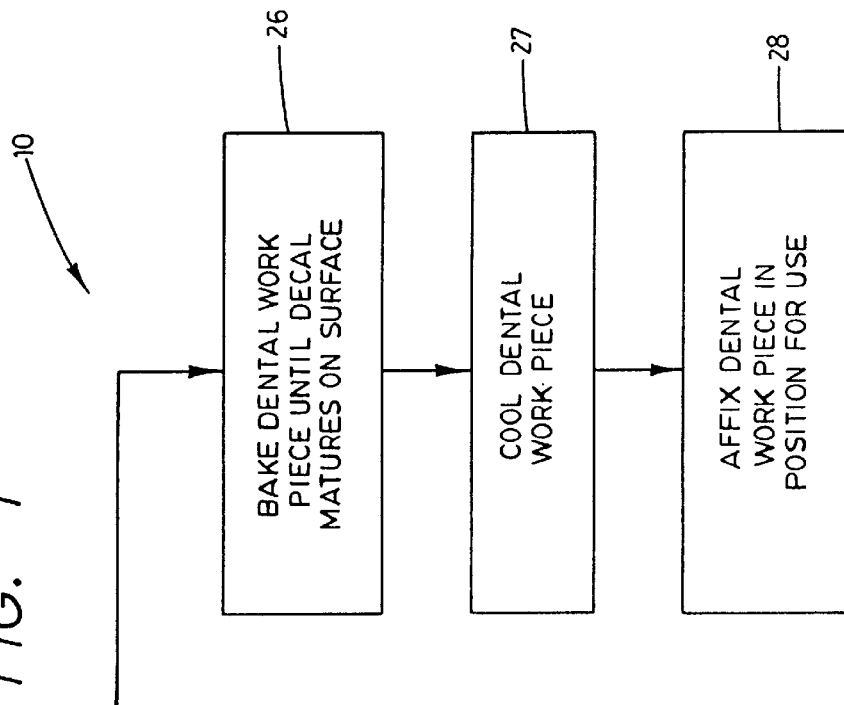

METHOD FOR AFFIXING A VISUAL ELEMENT ON A DENTAL WORKPIECE

CROSS-REFERENCE TO RELATED APPLICATIONS

Not Applicable.

STATEMENT REGARDING FEDERALLY SPONSORED RESEARCH OR DEVELOPMENT

Not Applicable.

BACKGROUND OF THE INVENTION

1. Field of the Invention

The present invention relates to a method for affixing a visual element on a workpiece and, more particularly, to such a method which has particular utility in applying decorative features to dental appliances.

2. Description of the Prior Art

The application of decorative works to the human body has been known in virtually all cultures throughout history and typically includes the use of various body paints, stains, and the like for topical application as well as invasive applications, such as using various tattooing or scaring procedures. Certain of these prior art practices produce a largely permanent result while others are temporary or subject gradually to dissipation over time.

The content of such decorative applications have included subject matter of virtually all types including those of religious, political, cultural and purely aesthetic character. While the content may vary, the inherent desire to adorn the human body in such a manner appears to be universal.

This same motivation has caused periodic experimentation with the application of such decorative subject matter to the teeth, but such experimentation has been largely without practical success due to the incompatibility of the teeth and the mouth with the procedures conventionally employed. It has, for example, been known to hand paint decorative features on teeth, or dental appliances. However, such conventional procedures produce decorative features which rapidly degrade because of the environment. More durable materials which otherwise would be employed in such conventional procedures, cannot be utilized due to the toxic nature of such substances. Other types of conventional procedures have, from time to time, been considered or used on a limited basis, but similarly without success.

Therefore, it has been recognized that it would be desirable to have a method for affixing a visual element on a workpiece having application to a wide variety of operative environments; which has particular utility in applying visual elements to workpieces intended for use under such circumstances as conventionally cause rapid deterioration of such visual elements; which is unusually well suited to affixing decorative elements and images on dental appliances adapted for emplacement in the mouth of a subject; which operates to ensure that such decorative elements are resistant to deterioration or other damage over a long operational life; which is not hazardous to the person using the decorative element; and which is otherwise entirely successful in achieving its operational objectives.

BRIEF SUMMARY OF THE INVENTION

Therefore, it is an object of the present invention to provide an improved method for affixing a visual element on a workpiece.

Another object is to provide such a method which has application to a wide variety of operative environments while possessing a simplicity and dependability of use.

Another object is to provide such a method which has particular utility in affixing decorative elements, such as art work including depictions of virtually all types of ornamental images, messages, trademarks, cartoon characters, and other decorative features, on dental appliances and the like.

Another object is to provide such a method which is unusually well suited to affixing decorative elements on porcelain tooth crowns prior to emplacement while being fully compatible with conventional materials and processes used in the production and emplacement of such porcelain dental crowns.

Another object is to provide such a method which results in the production of a porcelain crown bearing a decorative image which is of extremely durable character resistant to the normal conditions of use which would, using conventional procedures, rapidly cause degradation of the image.

Another object is to provide such a method which results in the manufacture of a dental appliance bearing a decorative image or the like which is not toxic to the person using the appliance.

Another object is to provide such a method which is inexpensive to use in the production of the resultant workpiece while possessing a virtually unlimited adaptability to the decorative and other visual elements to be affixed to the workpiece.

Further objects and advantages are to provide improved procedures in a method for the purposes described which is dependable, economical, produces a durable resultant product and which is otherwise fully effective in accomplishing its intended purposes.

These and other objects and advantages are achieved, in the preferred embodiment of the present invention, in a method for affixing a visual element on a workpiece, the method including the steps of selecting a visual element to be affixed on the workpiece; treating the visual element so as to render it transferable to the workpiece; transferring the visual element onto the workpiece in a target position thereon; and curing the visual element on the workpiece in the target position so as to affix the visual element in the target position thereon.

BRIEF DESCRIPTION OF THE SEVERAL VIEWS OF THE DRAWINGS

FIG. 1 is a schematic diagram of the steps in the method of the preferred embodiment of the method of the present invention.

FIG. 2 is a perspective view of a typical workpiece, in this case a porcelain dental crown, bearing a visual element illustrative of a resultant workpiece produced in the practice of the method of the present invention.

DETAILED DESCRIPTION OF THE INVENTION

Referring more particularly to the drawings, the method of the present invention is generally indicated by the numeral 10 in FIG. 1. It will be understood that the specific steps in the method shown in FIG. 1 is merely representative of a wide variety of specific embodiments of the invention and the subject invention is not limited thereto.

As shown in FIG. 1, the first step in the method of the preferred embodiment of the subject invention is generally indicated by the numeral 21. The first step of the method calls for the selection of a dental decal which is to be affixed to the workpiece in accordance with the method of the present invention. Other types of visual elements can be employed other than decals, but as will subsequently be seen a decal is particularly well suited to usage in the method of the present invention.

The particular decal employed can be of any desired type bearing the desired visual element, which can be of any type while being of a relatively small size suitable for being affixed on the particular workpiece involved. More specifically, the decal consists of a transparent transfer on which the particular visual element or image has been imprinted or otherwise affixed. The transfer is borne by a backing from which it is removable as a result of soaking in a suitable liquid, such as water. Where the particular workpiece involved is a dental appliance, such as a dental crown, the decal is of small size; that is, about three (3) to eight (8) millimeters in width and length.

Unlike conventional decals, in accordance with the method 10 of the present invention, the particular decorative feature or image borne by the transfer is produced using colored dental stains approved for use in the mouth of the subject in which the dental appliance is to be emplaced. Thus, the dental stains are those approved for use by, for example, the American Dental Society which are nontoxic in character, but which are of a durable nature impervious to attack by the substances to which they are subjected during use. Similarly, the dental stains employed are resistant to wear or other physical contact which are also encountered during use.

As to the specific visual element borne by the transfer, any visual element can be employed limited only by the size of the decal as controlled by the size of the dental appliance to which it is to be affixed. Purely for purposes of illustrative convenience, images such as those of a colorful and attractive nature, or employed to convey a message, either directly or indirectly, can be employed. Illustrative of such images are, for example, images of a butterfly, a flower, a cartoon character, a trademark, a rainbow, or virtually any other type of image.

The second step in the method 10 of the present invention is generally indicated by the numeral 22 in FIG. 1. In the second step, the decal selected in the first step 21 of the method is immersed in a liquid bath and permitted to soak for a period of time sufficient to render the transfer removable from the backing of the decal. The liquid bath can be of any suitable liquid, such as water or another solution suitable for causing this release to take place.

The third step in the method of the present invention is generally indicated by the numeral 23 in FIG. 1. The third step calls for the decal, subsequent to soaking in the liquid bath, to be removed from the backing of the decal. Such removal can be done by hand or by any other suitable means. Typically, such removal is performed by placing the backing bearing the transfer, subsequent to soaking in the liquid bath, in juxtaposition to the dental workpiece to which it is to be applied.

The fourth step in the method 10 of the present invention is generally indicated by the numeral 24 in FIG. 1. The fourth step calls for the transfer of the decal to be applied to the surface of the dental workpiece. As noted in relation to the third step of the method, this is performed typically by placing the backing in juxtaposition to the particular dental workpiece and sliding the transfer from the backing onto the surface of the dental workpiece. The transfer is moved toward and into registry with a target position on the dental workpiece. The target position, in the case of a porcelain crown, is typically an outer side surface of the porcelain crown generally centered relative thereto. In addition to placing the transfer in registry with the target position on the dental workpiece, the transfer is oriented within the target position to place the visual image borne thereby in the desired attitude. It will be understood that in the case of other types of workpieces, the particular target position and orientation may be different than that heretofore described with respect to a workpiece consisting of a porcelain crown.

The fifth step in the method 10 of the present invention is generally indicated by the numeral 25 in FIG. 1. In the fifth step of the method, the transfer or decal, which is moist due to being immersed in the liquid bath in the second step of the method, is dried on the surface of the dental workpiece. This is preferably achieved by placing the workpiece, bearing the transfer or decal, in a dental furnace heated to a temperature of approximately twelve hundred degrees Fahrenheit (1200° F.), for a period of time, such as about five (5) minutes, as necessary to remove the unwanted moisture causing the decal to adhere to the surface of the dental workpiece in the target position oriented as previously described with respect to the fourth step 24 of the method.

Upon completion of the fifth step 25, in the sixth step 26 the dental workpiece is retained in the dental furnace and is baked causing the decal, or transfer, to become permanently affixed in the target position and in the described orientation on the dental workpiece. The temperature and period of time required to achieve this sixth step can vary depending upon the particular workpiece involved and the specific decal or transfer involved. However, in the case of a porcelain crown, this step may be performed by increasing the temperature within the dental furnace from the prevailing twelve hundred degrees Fahrenheit (1200° F.) to eighteen hundred degrees Fahrenheit (1800° F.) at the rate of about one hundred degrees Fahrenheit (100° F.) per minute. Upon completion of the sixth step of the method, the image borne by the decal is permanently affixed to the dental workpiece in the target position and in the orientation selected.

The seventh step in the method is generally indicated by the numeral 27 in FIG. 1. The seventh step simply involves permitting the dental workpiece to cool to approximately ambient temperature. This may best be achieved by simply exposing the dental workpiece to the ambient atmosphere so as not to cause damage either to the dental workpiece or to the decal by accelerated cooling thereof.

The eighth step in the method of the present invention is generally indicated by the numeral 28 in FIG. 1. The eighth step calls for the dental workpiece, bearing the decal, to be emplaced in the patient's mouth at the predetermined location and in accordance with proper dental practice. Thus, in the case of a porcelain crown, the crown is cemented in position on the tooth, remanent of the tooth, or implant in the predetermined location and with the decal displayed as originally intended.

For illustrative convenience, a dental workpiece, or porcelain crown, is shown in FIG. 2 generally indicated by the numeral 40. The depiction of FIG. 2 is provided simply to illustrate one such resultant workpiece produced using the method of the present invention. As shown therein, the porcelain crown has a side wall 41, an upper wall 42 and a lower boundary 43 which, after the completion of the eighth step 28 of the method of the present invention is disposed in juxtaposition to the gum line of the patient. The porcelain crown can also be visualized as having an outer surface 44.

As also shown in FIG. 2 also for illustrative convenience, a transfer or decal is generally indicated by the numeral 50 and has an outer surface 51 and an opposite inner surface 52. The decal has a peripheral edge 53. The decal bears a visual element, decorative element, visual image or other image generally indicated by the numeral 54. It will be understood that once the practice of the method of the present invention has been completed, the only visible portion of the decal 50 is the visual element 54 since the decal itself is otherwise transparent and the peripheral edge 53 is not visible.

While other types of workpieces can be employed in the practice of the method of the present invention, in the specific illustrative embodiment shown in FIG. 2, it will be understood that the porcelain crown 40 is not on a tooth readily visible in the patient's mouth. This is intentional in that the patient can control whether the visual element is made visible to others since exposure to others requires that the mouth of the patient be positioned so as to achieve such exposure.

Since the visual element or image is formed entirely from nontoxic dental stains approved for usage in the mouth, no adverse consequences result from such usage. Similarly, the visual image, in the case of the decals, is typically formed on the inner surface 52 of the transfer or decal. Thus, the visual image is captured between the transfer and the side wall 41 of the porcelain crown. Finally, the baking of the dental workpiece bearing the decal causes the image to mature on the surface of the porcelain crown, thereby making it a permanent image resistant to both the substances to which it is exposed, as well as to wear during normal use.

Therefore, the method of the present invention is particularly well suited to affixing a visual element on a workpiece and has application to a wide variety of operative environments; has particular utility in applying visual elements to workpieces intended for use under circumstances which conventionally rapidly cause deterioration of such visual elements; is unusually well suited to affixing decorative elements on dental appliances adapted for emplacement in the mouth of a subject; operates to ensure that such decorative elements are resistant to deterioration or other damage over a long operational life; is not hazardous to the person using the decorative element; and is otherwise entirely successful in achieving its operational objectives.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. A method for affixing a visual element on a workpiece, wherein said workpiece is a porcelain crown, the method comprising the steps of:

selecting a visual element to be affixed on the workpiece;

treating said visual element so as to render it transferable to the workpiece;

transferring said visual element onto the workpiece in a target position thereon wherein said target position is on a side surface thereof; and curing said visual element on the workpiece including drying the visual element in said target position so as to affix the visual element in said target position thereon.

2. A method for affixing a visual element on a workpiece, the method comprising the steps of:

selecting a visual element to be affixed on the workpiece, wherein said selecting step includes selecting a visual element consisting of a decal bearing a decorative feature formed from nontoxic dental stains;

treating said visual element so as to render it transferable to the workpiece;

transferring said visual element onto the workpiece in a target position thereon; and curing said visual element on the workpiece in said target position and, wherein said curing step includes drying the visual element in the target position on the workpiece in a dental furnace, so as to affix the visual element in said target position on the workpiece.

3. A method for affixing a decorative element on a dental appliance, such as a porcelain crown or the like adapted for emplacement in a predetermined position in the mouth of a living creature, the method comprising the steps of:

A. selecting a target position on the dental appliance for affixing the decorative element which is capable of being visible in said predetermined position;

B. selecting a decorative element for affixing in said target position which is composed of a decal, bearing a decorative feature, borne by a backing from which said decal is adapted to be released upon exposure to liquid;

C. immersing said decorative element in a liquid bath for a period of time sufficient to permit release of the decal from the backing thereof;

D. transferring the decal from the backing to the target position on the dental appliance oriented so as to display the decorative feature thereof in the desired manner and so that the decal adheres to the dental appliance in said target position and as so oriented;

E. applying heat to the dental appliance in a dental furnace for a period of time sufficient to dry the decal in said target position and as so oriented on the dental appliance;

F. baking the dental appliance for a period of time and at a temperature sufficient to cause said decal to mature on the dental appliance in said target position and as so oriented;

G. cooling the dental appliance to substantially ambient temperature in such a manner as to cause said decorative feature to be displayed in the target position on the dental appliance substantially without degradation thereof; and H. mounting the dental appliance in the mouth of said living creature in said predetermined position whereby said decorative feature is exposable to view.

4. The method of claim 3 wherein said dental appliance is a porcelain crown, said predetermined position is a molar tooth, remnant thereof, or implant occupying the position of a molar tooth and said target position is a side surface of said porcelain crown exposed to visibility substantially within the voluntary action of the living creature.

* * * * *